（12）United States Patent
Shi (10) Patent No.: US 10,571,416 B2
(45) Date of Patent: Feb. 25, 2020

(54) SOLAR BIOELECTRICAL IMPEDANCE SPECTROMETER AND BIOELECTRICAL IMPEDANCE MONITORING SYSTEM HAVING SAME

(71) Applicant: Xiaoli Shi, Dazhou (CN)

(72) Inventor: Xiaoli Shi, Dazhou (CN)

(73) Assignee: SHENZHEN DANSHA TECHNOLOGY CO., LTD., Shenzhen, Guangdong (CN)

( * ) Notice: Subject to any disclaimer, the term of this patent is extended or adjusted under 35 U.S.C. 154(b) by 343 days.

(21) Appl. No.: 15/702,771

(22) Filed: Sep. 13, 2017

(65) Prior Publication Data

US 2018/0003657 A1    Jan. 4, 2018

(51) Int. Cl.
*G01N 27/02*  (2006.01)
*A61B 5/053*  (2006.01)
*H02S 40/38*  (2014.01)
*H02S 99/00*  (2014.01)
*A61B 5/00*  (2006.01)

(52) U.S. Cl.
CPC ............ *G01N 27/02* (2013.01); *A61B 5/002* (2013.01); *A61B 5/0004* (2013.01); *A61B 5/053* (2013.01); *A61B 5/7257* (2013.01); *A61B 5/7264* (2013.01); *H02S 40/38* (2014.12); *H02S 99/00* (2013.01); *A61B 2560/0214* (2013.01)

(58) Field of Classification Search
CPC ......... G01N 27/02; H02S 99/00; H02S 40/38; A61B 5/053; A61B 5/0004; A61B 5/7264; A61B 5/7257; A61B 5/002; A61B 2560/0214; A61B 5/4875; A61B 2562/18; A61B 5/4869
See application file for complete search history.

(56) References Cited

U.S. PATENT DOCUMENTS

| 10,154,460 | B1* | 12/2018 | Miller | H04W 52/0254 |
|---|---|---|---|---|
| 2013/0248695 | A1* | 9/2013 | Macintyre | A61B 5/1455 250/227.11 |
| 2014/0275843 | A1* | 9/2014 | Piccirillo | A61B 5/14556 600/301 |
| 2016/0331314 | A1 | 11/2016 | Bhansali et al. | |

FOREIGN PATENT DOCUMENTS

| CN | 202821350 U | 3/2013 |
|---|---|---|
| CN | 103278538 A * | 9/2013 |

* cited by examiner

*Primary Examiner* — Huy Q Phan
*Assistant Examiner* — Zannatul Ferdous (57) ABSTRACT

A solar bioelectrical impedance spectrometer includes a microprocessor module, a radio module connected with the microprocessor module, a spectrometer module connected with the microprocessor module, a battery management module, a battery module connected with the battery management module, a solar power supply management module separately connected with the battery management module and the microprocessor module and a wearable solar cell module connected with the solar power supply management module. The battery management module is configured for receiving current output from the solar power supply management module under a preset condition and charging the battery module by the current. The spectrometer module includes an impedance network analyzer, a differential amplifier connected with the impedance network analyzer, and a wide-band current source connected with the impedance network analyzer.

20 Claims, 4 Drawing Sheets

SOLAR BIOELECTRICAL IMPEDANCE SPECTROMETER AND BIOELECTRICAL IMPEDANCE MONITORING SYSTEM HAVING SAME

FIELD OF THE PATENT APPLICATION

The present patent application generally relates to medical electronics and more specifically to a solar bioelectrical impedance spectrometer and a bioelectrical impedance monitoring system having the same.

BACKGROUND

Bioelectrical impedance analysis (BIA) is a noninvasive, safe, inexpensive and portable technique for rapid assessment of body composition and body water that requires minimal patient collaboration. BIA measures the voltage and phase angle of a signal generated by injecting a small sinusoidal electrical current at a single or multiple frequencies into the body, typically from hand to foot and computes the complex impedance values, with the real part of the impedance representing resistance (R) and the imaginary part of the impedance representing the reactance (Xc).

Multi-frequency analysis is used to determine the amount of extracellular (ECW) and intracellular water (ICW) based on a simple model of a purely capacitive membrane separating a resistive intra and extracellular space. Therefore ECW can be estimated from the impedance at low frequency and total body water (TBW) from the real component of the impedance at high frequency where the capacitive effect of the cell membrane can be neglected. ICW can be calculated from the difference between TBW and ECW.

In contrast to BIA, bioelectrical impedance vector analysis (BIVA) does not require any assumption about body geometry, electrical tissue models or regression analysis. In the BIVA representation body composition is described as a vector with resistance (R) as the abscissa, and reactance (Xc) as the ordinate normalized by the subject's height (H). To achieve a wider use of BIA/BIVA applications and to promote the use of BIA technology by patients and health care providers with limited training, it is desired to have a portable, low cost, battery operated and durable multi-frequency impedance spectrometer.

SUMMARY

The present patent application is directed to a solar bioelectrical impedance spectrometer and a bioelectrical impedance monitoring system having the same. In one aspect, the solar bioelectrical impedance spectrometer includes: a microprocessor module; a radio module connected with the microprocessor module; a spectrometer module connected with the microprocessor module; a battery management module; a battery module connected with the battery management module; a solar power supply management module separately connected with the battery management module and the microprocessor module; and a wearable solar cell module connected with the solar power supply management module. The battery management module is configured for receiving current output from the solar power supply management module under a preset condition and charging the battery module by the current. The spectrometer module includes an impedance network analyzer, a differential amplifier connected with the impedance network analyzer, and a wide-band current source connected with the impedance network analyzer. The solar power supply management module incudes a first switch connected with the wearable solar cell module; an enhancement circuit connected with the first switch; a first diode connecting the enhancement circuit with the spectrometer module; a control voltage generator connected with the wearable solar battery module; a second diode connecting the control voltage generator with the spectrometer module; a second switch connected with the wearable solar battery module; a transistor, of which the gate is connected with the control voltage generator and the drain or source is connected with the second switch; a third diode connecting the source or the drain of the transistor with the spectrometer module; a third switch connecting the control voltage generator with the spectrometer module; a fourth switch connected with the wearable solar battery module; and a fourth diode connecting the fourth switch with the spectrometer module. The battery management module is connected with the second diode and the control voltage generator. The microprocessor module is configured to calculate a reference voltage value according to the output voltage of the wearable solar battery module and determine and control on/off states of the first switch, the second switch, the third switch and the fourth switch according to the reference voltage value. When the reference voltage value is lower than a first voltage threshold, the microprocessor module is configured to turn on the first switch and turn off the other three switches at the same time. When the reference voltage value reaches or exceeds the first voltage threshold and is lower than a second voltage threshold, the microprocessor module is configured to turn on the fourth switch and turn off the other three switches at the same time. When the reference voltage value reaches or exceeds the second voltage threshold, the microprocessor module is configured to turn on the second switch and the third switch, and turn off the other two switches at the same time.

The impedance network analyzer may include a 12-bit analog to digital converter (ADC) configured to sample and digitize the input signal at a rate of 1 MSPS and an integrated DSP configured to apply a Discrete Fourier Transformation (DFT) to the digitized input signal and return real and imaginary components of the transformed signal, and may be configured to be programmed via an I2C bus.

The wide-band current source may include a differential receiver amplifier with a first input, a second input and an output; a unity gain amplifier connected between the second input of the differential receiver amplifier and the output of the differential receiver amplifier and forming a feedback loop; and an amplifier connected between the first input of the differential receiver amplifier and the output of the unity gain amplifier and forming a DC stable loop.

The wide-band current source may further include two resistors and tetrapolar electrodes, output of the differential receiver amplifier and output of the unity gain amplifier being coupled to the tetrapolar electrodes through the two resistors respectively.

The wide-band current source may further include two capacitors, output of the differential receiver amplifier and output of the unity gain amplifier being coupled to the tetrapolar electrodes through the two capacitors respectively.

The radio module may be configured to communicate with a mobile device via a Bluetooth connection and allow setting of measurement parameters from the mobile device.

In another aspect, the present patent application provides a bioelectrical impedance monitoring system including: a solar bioelectrical impedance spectrometer; a mobile device in communication with the solar bioelectrical impedance spectrometer; and a central server in communication with the mobile device. The solar bioelectrical impedance spectrometer is configured for measuring bioelectrical impedance of a user and transmitting data related to the bioelectrical impedance to the mobile device wirelessly. The mobile device is configured for running a graphical interface program and sending the data to the central server. The central server is configured to be accessed by a service provider so that the service provider correspondingly sends feedback to the user. The solar bioelectrical impedance spectrometer includes: a microprocessor module; a radio module connected with the microprocessor module; a spectrometer module connected with the microprocessor module; a battery management module; a battery module connected with the battery management module; a solar power supply management module separately connected with the battery management module and the microprocessor module; and a wearable solar battery module connected with the solar power supply management module. The solar power supply management module includes: a first switch connected with the wearable solar battery module; an enhancement circuit connected with the first switch; a first diode connecting the enhancement circuit with the spectrometer module; a control voltage generator connected with the wearable solar battery module; a second diode connecting the control voltage generator with the spectrometer module; a second switch connected with the wearable solar battery module; a transistor, of which the gate is connected with the control voltage generator and the drain or source is connected with the second switch; a third diode connecting the source or the drain of the transistor with the spectrometer module; a third switch connecting the control voltage generator with the spectrometer module; a fourth switch connected with the wearable solar battery module; and a fourth diode connecting the fourth switch with the spectrometer module. The battery management module is connected with the second diode and the control voltage generator. The microprocessor module calculates a reference voltage value according to the output voltage of the wearable solar battery module and determines and controls the on/off states of the first switch, the second switch, the third switch and the fourth switch according to the reference voltage value.

The spectrometer module may include an impedance network analyzer, a differential amplifier connected with the impedance network analyzer, and a wide-band current source connected with the impedance network analyzer.

When the reference voltage value is lower than a first voltage threshold, the microprocessor module may turn on the first switch and turn off the other three switches at the same time. When the reference voltage value reaches or exceeds the first voltage threshold and is lower than a second voltage threshold, the microprocessor module may turn on the fourth switch and turn off the other three switches at the same time. When the reference voltage value reaches or exceeds the second voltage threshold, the microprocessor module may turn on the second switch and the third switch and turn off the other two switches at the same time.

In yet another aspect, the present patent application provides a solar bioelectrical impedance spectrometer including: a microprocessor module; a radio module connected with the microprocessor module; a spectrometer module connected with the microprocessor module; a battery management module; a battery module connected with the battery management module; a solar power supply management module separately connected with the battery management module and the microprocessor module; and a wearable solar cell module connected with the solar power supply management module. The battery management module is configured for receiving current output from the solar power supply management module under a preset condition and charging the battery module by the current. The spectrometer module includes an impedance network analyzer, a differential amplifier connected with the impedance network analyzer, and a wide-band current source connected with the impedance network analyzer.

The solar power supply management module may include: a first switch connected with the wearable solar cell module; an enhancement circuit connected with the first switch; a first diode connecting the enhancement circuit with the spectrometer module; a control voltage generator connected with the wearable solar battery module; a second diode connecting the control voltage generator with the spectrometer module; a second switch connected with the wearable solar battery module; a transistor, of which the gate is connected with the control voltage generator and the drain or source is connected with the second switch; a third diode connecting the source or the drain of the transistor with the spectrometer module; a third switch connecting the control voltage generator with the spectrometer module; a fourth switch connected with the wearable solar battery module; and a fourth diode connecting the fourth switch with the spectrometer module.

The battery management module may be connected with the second diode and the control voltage generator. The microprocessor module may be configured to calculate a reference voltage value according to the output voltage of the wearable solar battery module and determine and control on/off states of the first switch, the second switch, the third switch and the fourth switch according to the reference voltage value.

When the reference voltage value is lower than a first voltage threshold, the microprocessor module may be configured to turn on the first switch and turn off the other three switches at the same time. When the reference voltage value reaches or exceeds the first voltage threshold and is lower than a second voltage threshold, the microprocessor module may be configured to turn on the fourth switch and turn off the other three switches at the same time. When the reference voltage value reaches or exceeds the second voltage threshold, the microprocessor module may be configured to turn on the second switch and the third switch and turn off the other two switches at the same time.

The impedance network analyzer may include a 12-bit analog to digital converter (ADC) configured to sample and digitize the input signal at a rate of 1 MSPS and an integrated DSP configured to apply a Discrete Fourier Transformation (DFT) to the digitized input signal and return real and imaginary components of the transformed signal, and may be configured to be programmed via an I2C bus.

The wide-band current source may include: a differential receiver amplifier with a first input, a second input and an output; a unity gain amplifier connected between the second input of the differential receiver amplifier and the output of the differential receiver amplifier and forming a feedback loop; and an amplifier connected between the first input of the differential receiver amplifier and the output of the unity gain amplifier and forming a DC stable loop.

The wide-band current source may further include two resistors and tetrapolar electrodes, output of the differential receiver amplifier and output of the unity gain amplifier being coupled to the tetrapolar electrodes through the two resistors respectively.

DETAILED DESCRIPTION

Reference will now be made in detail to a preferred embodiment of the solar bioelectrical impedance spectrometer and the bioelectrical impedance monitoring system having the same disclosed in the present patent application, examples of which are also provided in the following description. Exemplary embodiments of the solar bioelectrical impedance spectrometer and the bioelectrical impedance monitoring system having the same disclosed in the present patent application are described in detail, although it will be apparent to those skilled in the relevant art that some features that are not particularly important to an understanding of the solar bioelectrical impedance spectrometer and the bioelectrical impedance monitoring system having the same may not be shown for the sake of clarity.

Furthermore, it should be understood that the solar bioelectrical impedance spectrometer and the bioelectrical impedance monitoring system having the same disclosed in the present patent application is not limited to the precise embodiments described below and that various changes and modifications thereof may be effected by one skilled in the art without departing from the spirit or scope of the protection. For example, elements and/or features of different illustrative embodiments may be combined with each other and/or substituted for each other within the scope of this disclosure.

Figure 1:
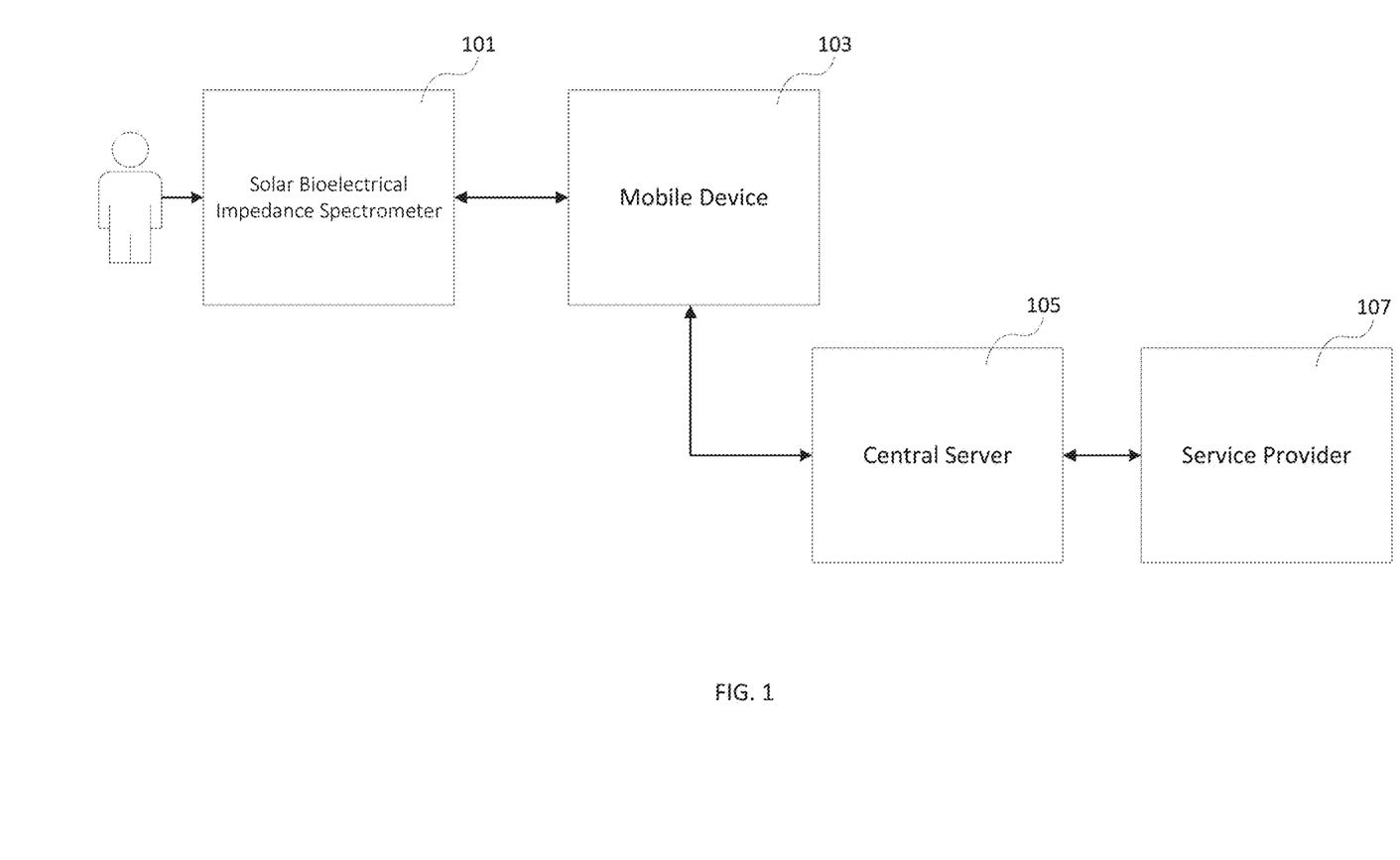
FIG. 1 is a block diagram of a bioelectrical impedance monitoring system in accordance with an embodiment of the present patent application.

FIG. 1 is a block diagram of a bioelectrical impedance monitoring system in accordance with an embodiment of the present patent application. Referring to FIG. 1, the bioelectrical impedance monitoring system includes a solar bioelectrical impedance spectrometer 101, a mobile device 103 in communication with the solar bioelectrical impedance spectrometer 101, and a central server 105 in communication with the mobile device 103. The solar bioelectrical impedance spectrometer 101 is configured to measure bioelectrical impedance of a user and transmit data related to the bioelectrical impedance to the mobile device 103 wirelessly. The mobile device 103 is configured to run a graphical application and send the data to the central server 105. A service provider 107, for example, a medical doctor, may access the data from the central server 105 and send feedback to the user accordingly.

In this embodiment, the solar bioelectrical impedance spectrometer 101 is configured to transmit data related to the bioelectrical impedance to the mobile device 103 through a Bluetooth connection. The mobile device 103 is a smart phone or a tablet computer.

Figure 2:
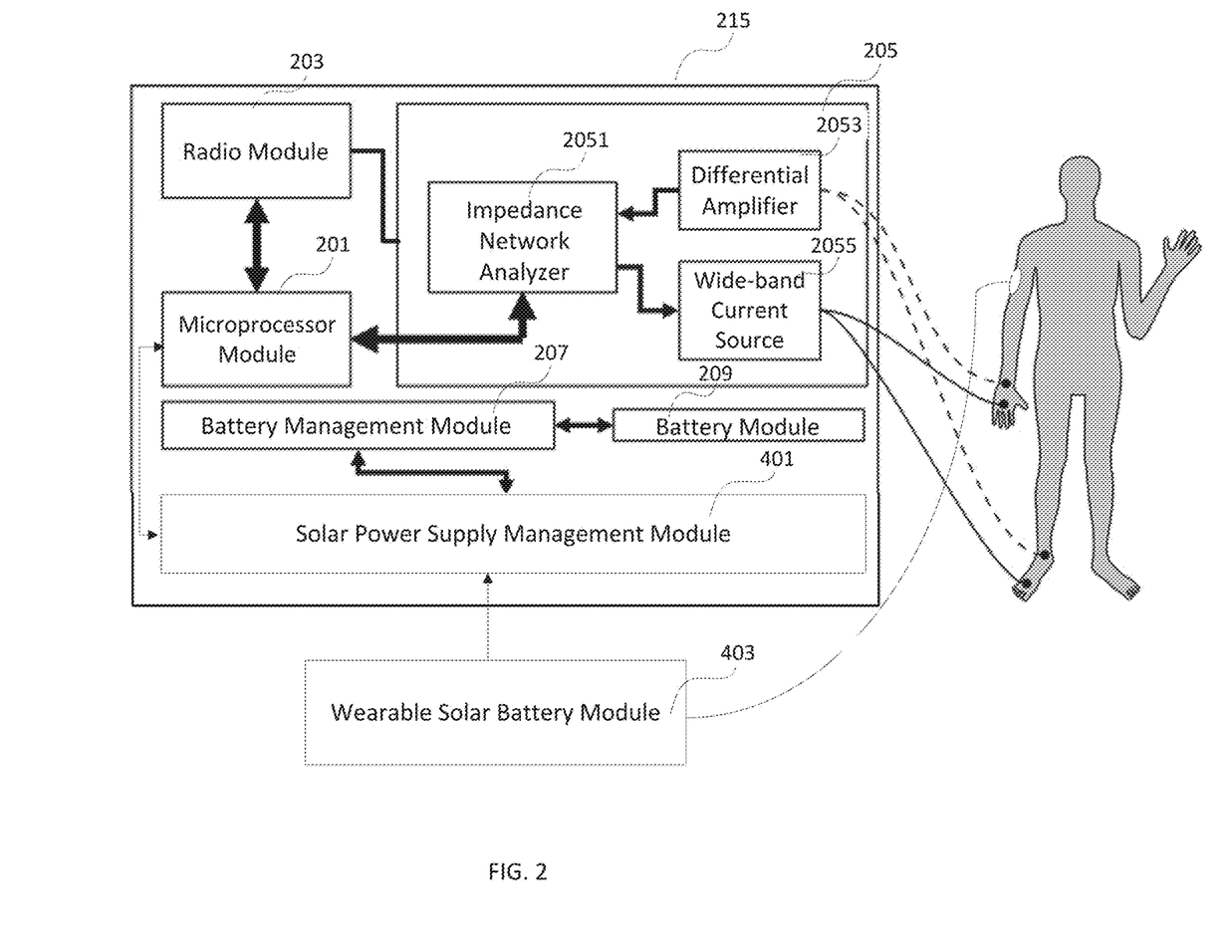
FIG. 2 is a block diagram of a solar bioelectrical impedance spectrometer as depicted in FIG. 1.

FIG. 2 is a block diagram of the solar bioelectrical impedance spectrometer 101 as depicted in FIG. 1. Referring to FIG. 2, the solar bioelectrical impedance spectrometer 101 includes a microprocessor module 201, a radio module 203 connected with the microprocessor module 201, a spectrometer module 205 connected with the microprocessor module 201, a battery management module 207, a battery module 209 connected with the battery management module 207, a solar power supply management module 401 connected with the battery management module 207 and the microprocessor module 201, and a wearable solar battery module 403 connected with the solar power supply management module 401. In this embodiment, the solar bioelectrical impedance spectrometer 101 further includes a casing 215. The casing 215 is a dust and water proof enclosure configured to ensure proper device functionality in harsh environments.

The radio module 203 is configured to communicate with the mobile device via a Bluetooth v2.1 connection and allow the mobile device to set measurement parameters of the solar bioelectrical impedance spectrometer 101, such as excitation amplitude, start and stop frequency and frequency increment.

The battery management module 207 is configured to receive electrical current from the solar power supply management module 401 under a preset condition, and charge the battery module 209 with the electrical current.

The spectrometer module 205 includes an impedance network analyzer 2051, a differential amplifier 2053 connected with the impedance network analyzer 2051, and a wide-band current source 2055 connected with the impedance network analyzer 2051. The differential amplifier 2053 and the wide-band current source 2055 are components of a front end circuit of the solar bioelectrical impedance spectrometer, which will be described in more detail hereafter. In this embodiment, the high precision digital impedance network analyzer 2501 is a fully integrated impedance analyzer with a build in frequency generator configured to determine an impedance over a wide range of selectable frequencies. The impedance network analyzer 2051 includes a 12-bit analog to digital converter (ADC) configured to sample and digitize the input signal at a rate of 1 MSPS and an integrated DSP configured to apply a discrete Fourier transformation (DFT) to the digitized input signal and return real and imaginary components of the transformed signal. The impedance network analyzer 2051 can be programmed via an I2C bus.

Figure 3:
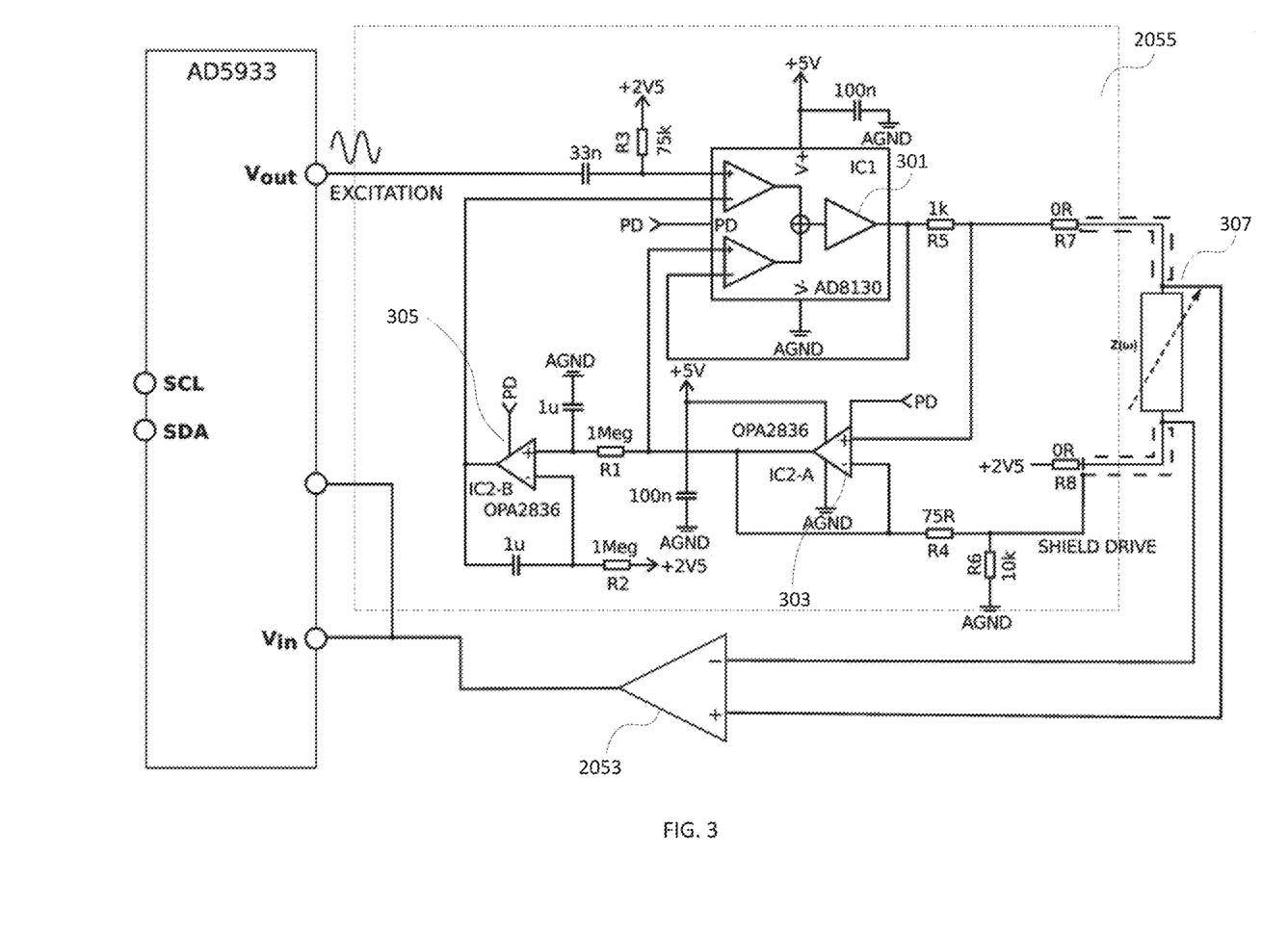
FIG. 3 is a circuit schematic diagram of a front end circuit of the solar bioelectrical impedance spectrometer as depicted in FIG. 2.

FIG. 3 is a circuit schematic diagram of a front end circuit of the solar bioelectrical impedance spectrometer as depicted in FIG. 2. Referring to FIG. 2 and FIG. 3, the front end circuit includes a wide-band current source 2055 and a differential amplifier 2053. The wide-band current source 2055 includes a differential receiver amplifier 301 (AD8130 in this embodiment) with a first input, a second input and an output, a unity gain amplifier 303 (OPA 2386 in this embodiment) connected between the second input of the differential receiver amplifier 301 and the output of the differential receiver amplifier 301 forming a feedback loop, and an amplifier 305 (OPA 2386 in this embodiment) connected between the first input of the differential receiver amplifier 301 and the output of the unity gain amplifier 303, forming a DC stabilization loop.

The wide-band current source 2055 further includes two resistors (R7 and R8) and tetrapolar electrodes 307. The output of the differential receiver amplifier 301 and the output of the unity gain amplifier 303 are coupled to the tetrapolar electrodes 307 through the two resistors R7 and R8 respectively.

The wide-band current source 2055 is configured to overcome output impedance limitations and allow precise tetrapolar impedance measurements. The differential receiver amplifier 301 has high CMRR (80 db@2 MHz) at high frequencies with a comparatively high input bias current of maximal 3.5 A. The unity gain amplifier 303 in the feedback loop overcomes high input bias current of maximal 3.5 A. The DC stabilization loop formed by the amplifier 305 allows single supply operation of the current source as well as for purely capacitive or ac coupled loads. The cut-off frequency of the DC stabilization loop is chosen small enough (below 0.5 Hz) to have a negligible effect on bioelectrical impedance measurements.

Referring to FIG. 3, in another embodiment, the output of the front end circuit may be ac coupled by replacing resistors R7 and R8 with suitable coupling capacitors, in order to achieve a fully bipolar current source. The maximum possible output current with the front end circuit is limited by the maximum output voltage swing of the differential receiver amplifier 301 and the current sense resistor R5 to 1.7 mA.

In the above embodiments, the differential receiver amplifier 301 has a comparatively high input bias current, Which may pose a problem since it affects the output current for small excitation signals and prevents accurate impedance measurements. However, such a problem is solved by the feedback loop formed by the unity gain amplifier 303. In addition, the DC stabilization loop formed by the amplifier 305 allows single supply operation of the current source as well as purely capacitive or ac coupled loads.

Figure 4:
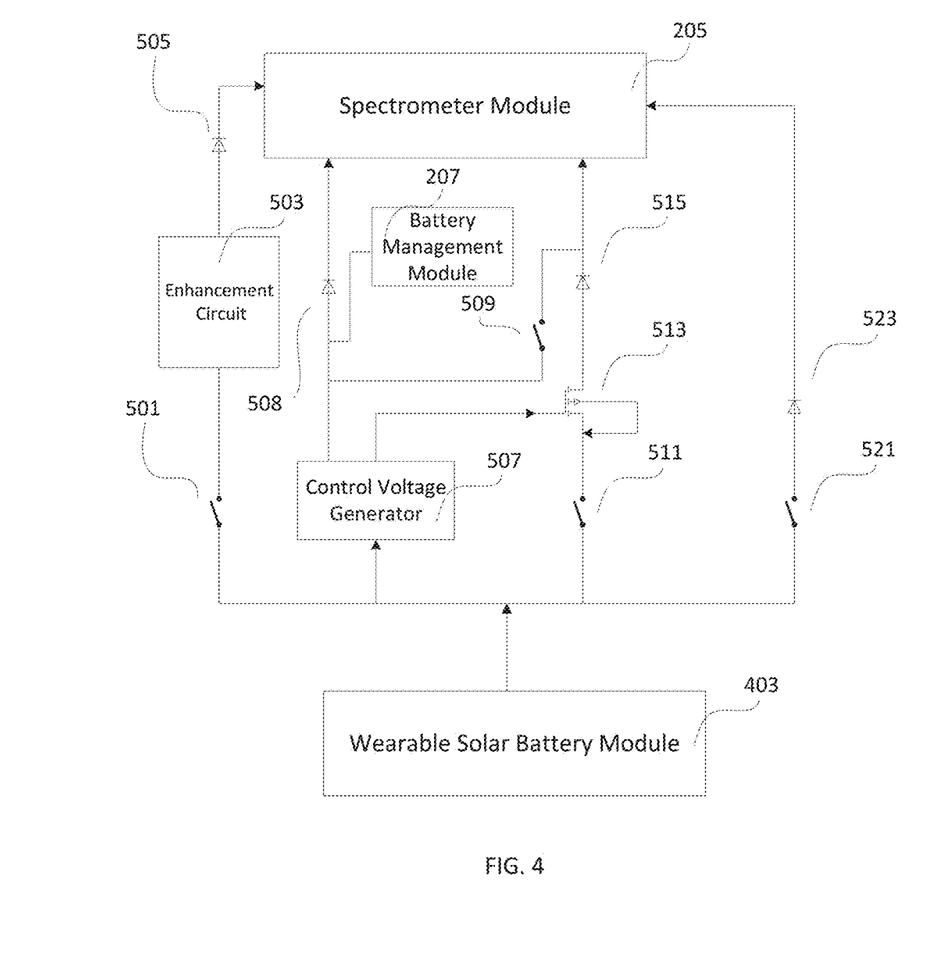
FIG. 4 is a circuit schematic diagram of a solar power supply management module as depicted in FIG. 2.

FIG. 4 is a circuit schematic diagram of the solar power supply management module 401 as depicted in FIG. 2. Referring to FIG. 4, the solar power supply management module 401 includes a first switch 501 connected with the wearable solar cell module 403; an enhancement circuit 503 connected with the first switch 501; a first diode 505 connecting the enhancement circuit 503 with the spectrometer module 205; a control voltage generator 507 connected with the wearable solar cell module 403; a second diode 508 connecting the control voltage generator 507 with the spectrometer module 205; a second switch 511 connected with the wearable solar battery module 403; a transistor 513, of which the gate is connected with the control voltage generator 507 and the drain or source is connected with the second switch 511; a third diode 515 connecting the source or drain of the transistor 513 with the spectrometer module 205; a third switch 509 connecting the control voltage generator 507 with the spectrometer module 205; a fourth switch 521 connected with the wearable solar battery module 403; and a fourth diode 523 connecting the fourth switch 521 with the spectrometer module 205. The battery management module 207 is connected with the second diode 508 and the control voltage generator 507.

In this embodiment, the microprocessor module 201 calculates a reference voltage value Vr according to the output voltage of the wearable solar battery module 403 and determines and controls the on/off states of the first switch 501, the second switch 511, the third switch 509 and the fourth switch 521 according to the reference voltage value Vr.

When the Vr is lower than a first voltage threshold Vt1, the microprocessor module 201 turns on the first switch 501 and turns off the other three switches at the same time. At this point, the device is in a weak light environment, such as an indoor place. The enhancement circuit 503 is used for amplifying the output of the wearable solar battery module 403 and supplying power to the spectrometer module 205 through the amplified output. In this embodiment, the enhancement circuit 503 has an input voltage of 0.5-3V and an output voltage of 3V.

When the Vr reaches or exceeds the first voltage threshold Vt1 and is lower than a second voltage threshold Vt2, the microprocessor module 201 turns on the fourth switch 521 and turns off the other three switches at the same time. At this time, the device is in a slightly stronger light environment, such as an outdoor shade. The output of the wearable solar battery module 403 directly supplies power to the spectrometer module 205.

When the Vr reaches or exceeds the second voltage threshold Vt2, the microprocessor module 201 turns on the second switch 511 and the third switch 509, and turns off the other two switches at the same time. At this point, the device is in a relatively strong light environment, for example under outdoor sunlight. At this time, the wearable solar battery module 403 charges the battery management module 207 via the second switch 511, the transistor 513 and the third switch 509. The control voltage generator 507 dynamically adjusts the control voltage it outputs to the gate of the transistor 513 according to the output of the wearable solar battery module 403 and the charging current flowing through the third switch 509 so as to adjust the load of the wearable solar battery module 403 and to maximize the photoelectric conversion efficiency of the wearable solar battery module 403.

In the above embodiments, the solar power supply management module 401 can enhance the power supply signal when the light is relatively weak, directly supply power when the light is slightly stronger and charge the battery management module 207 when the light is relatively strong according to the output of the wearable solar battery module 403. In addition, when the light is relatively strong, the control voltage generator 507 can change its output to dynamically adjust the load of the wearable solar battery module 403 so as to optimize the photoelectric conversion efficiency of the wearable solar battery module 403. Therefore, in different light environments, the wearable solar battery module 403 can satisfy the power supply requirements of the bioelectrical impedance spectrometer with a relatively high efficiency.

In the above embodiments, the solar multi-frequency bioelectrical impedance spectrometer for BIA and BIVA applications is capable of tracking nutritional and hydration status in healthy subjects and patients. The simplicity of BIA/BIVA measurements and the simple visual representation of impedance data enable patients to compare and determine body composition during the time course of a specific treatment plan. Patients may be actively engaged in their health and take responsibility, leading to a higher adherence to the treatment plan. The solar bioelectrical impedance spectrometer may also be useful for early diagnosis. In addition, a medical care provider such as a doctor may access the data from the central server and send feedback to the user according to the measurements of the bioelectrical impedance spectrometer.

While the present patent application has been shown and described with particular references to a number of embodiments thereof, it should be noted that various other changes or modifications may be made without departing from the scope of the present invention.

What is claimed is:
1. A solar bioelectrical impedance spectrometer, comprising:
  a microprocessor module;
  a radio module connected with the microprocessor module;
  a spectrometer module connected with the microprocessor module;
  a battery management module;
  a battery module connected with the battery management module;

a solar power supply management module separately connected with the battery management module and the microprocessor module; and a wearable solar cell module connected with the solar power supply management module; wherein:

the battery management module is configured for receiving current output from the solar power supply management module under a preset condition and charging the battery module by the current;

the spectrometer module comprises an impedance network analyzer, a differential amplifier connected with the impedance network analyzer, and a wide-band current source connected with the impedance network analyzer;

the solar power supply management module comprises:

a first switch connected with the wearable solar cell module;

an enhancement circuit connected with the first switch;

a first diode connecting the enhancement circuit with the spectrometer module;

a control voltage generator connected with the wearable solar battery module;

a second diode connecting the control voltage generator with the spectrometer module;

a second switch connected with the wearable solar battery module;

a transistor, of which the gate is connected with the control voltage generator and the drain or source is connected with the second switch;

a third diode connecting the source or the drain of the transistor with the spectrometer module;

a third switch connecting the control voltage generator with the spectrometer module;

a fourth switch connected with the wearable solar battery module; and a fourth diode connecting the fourth switch with the spectrometer module;

the battery management module is connected with the second diode and the control voltage generator;

the microprocessor module is configured to calculate a reference voltage value according to the output voltage of the wearable solar battery module and determine and control on/off states of the first switch, the second switch, the third switch and the fourth switch according to the reference voltage value;

when the reference voltage value is lower than a first voltage threshold, the microprocessor module is configured to turn on the first switch and turn off the other three switches at the same time;

when the reference voltage value reaches or exceeds the first voltage threshold and is lower than a second voltage threshold, the microprocessor module is configured to turn on the fourth switch and turn off the other three switches at the same time; and when the reference voltage value reaches or exceeds the second voltage threshold, the microprocessor module is configured to turn on the second switch and the third switch, and turn off the other two switches at the same time.

2. The solar bioelectrical impedance spectrometer of claim 1, wherein the impedance network analyzer comprises a 12-bit analog to digital converter (ADC) configured to sample and digitize the input signal at a rate of 1 MSPS and an integrated DSP configured to apply a Discrete Fourier Transformation (DFT) to the digitized input signal and return real and imaginary components of the transformed signal, and is configured to be programmed via an I2C bus.

3. The solar bioelectrical impedance spectrometer of claim 1, wherein the wide-band current source comprises:

a differential receiver amplifier with a first input, a second input and an output;

a unity gain amplifier connected between the second input of the differential receiver amplifier and the output of the differential receiver amplifier and forming a feedback loop; and an amplifier connected between the first input of the differential receiver amplifier and the output of the unity gain amplifier and forming a DC stable loop.

4. The solar bioelectrical impedance spectrometer of claim 3, wherein the wide-band current source further comprises two resistors and tetrapolar electrodes, output of the differential receiver amplifier and output of the unity gain amplifier being coupled to the tetrapolar electrodes through the two resistors respectively.

5. The solar bioelectrical impedance spectrometer of claim 4, wherein the wide-band current source further comprises two capacitors, output of the differential receiver amplifier and output of the unity gain amplifier being coupled to the tetrapolar electrodes through the two capacitors respectively.

6. The solar bioelectrical impedance spectrometer of claim 1, wherein the radio module is configured to communicate with a mobile device via a Bluetooth connection and allow setting of measurement parameters from the mobile device.

7. A bioelectrical impedance monitoring system, comprising:

a solar bioelectrical impedance spectrometer;

a mobile device in communication with the solar bioelectrical impedance spectrometer; and a central server in communication with the mobile device; wherein:

the solar bioelectrical impedance spectrometer is configured for measuring bioelectrical impedance of a user and transmitting data related to the bioelectrical impedance to the mobile device wirelessly;

the mobile device is configured for running a graphical interface program and sending the data to the central server;

the central server is configured to be accessed by a service provider so that the service provider correspondingly sends feedback to the user;

the solar bioelectrical impedance spectrometer comprises:

a microprocessor module;

a radio module connected with the microprocessor module;

a spectrometer module connected with the microprocessor module;

a battery management module;

a battery module connected with the battery management module;

a solar power supply management module separately connected with the battery management module and the microprocessor module; and a wearable solar battery module connected with the solar power supply management module, wherein the solar power supply management module comprises:

a first switch connected with the wearable solar battery module;

an enhancement circuit connected with the first switch;

a first diode connecting the enhancement circuit with the spectrometer module;

a control voltage generator connected with the wearable solar battery module;

a second diode connecting the control voltage generator with the spectrometer module;

a second switch connected with the wearable solar battery module;

a transistor, of which the gate is connected with the control voltage generator and the drain or source is connected with the second switch;

a third diode connecting the source or the drain of the transistor with the spectrometer module;

a third switch connecting the control voltage generator with the spectrometer module;

a fourth switch connected with the wearable solar battery module; and a fourth diode connecting the fourth switch with the spectrometer module;

the battery management module is connected with e second diode and the control voltage generator; and the microprocessor module calculates a reference voltage value according to the output voltage of the wearable solar battery module and determines and controls the on/off states of the first switch, the second switch, the third switch and the fourth switch according to the reference voltage value.

8. The bioelectrical impedance monitoring system of claim 7, wherein the spectrometer module comprises an impedance network analyzer, a differential amplifier connected with the impedance network analyzer, and a wide-band current source connected with the impedance network analyzer.

9. The bioelectrical impedance monitoring system of claim 7, wherein when the reference voltage value is lower than a first voltage threshold, the microprocessor module turns on the first switch and turns off the other three switches at the same time.

10. The bioelectrical impedance monitoring system of claim 7, wherein when the reference voltage value reaches or exceeds the first voltage threshold and is lower than a second voltage threshold, the microprocessor module turns on the fourth switch and turns off the other three switches at the same time; and when the reference voltage value reaches or exceeds the second voltage threshold, the microprocessor module turns on the second switch and the third switch and turns off the other two switches at the same time.

11. A solar bioelectrical impedance spectrometer, comprising:

a microprocessor module;

a radio module connected with the microprocessor module;

a spectrometer module connected with the microprocessor module;

a battery management module;

a battery module connected with the battery management module;

a solar power supply management module separately connected with the battery management module and the microprocessor module; and a wearable solar cell module connected with the solar power supply management module; wherein:

the battery management module is configured for receiving current output from the solar power supply management module under a preset condition and charging the battery module by the current; and the spectrometer module comprises an impedance network analyzer, a differential amplifier connected with the impedance network analyzer, and a wide-band current source connected with the impedance network analyzer.

12. The solar bioelectrical impedance spectrometer of claim 11, wherein the solar power supply management module comprises:

a first switch connected with the wearable solar cell module;

an enhancement circuit connected with the first switch;

a first diode connecting the enhancement circuit with the spectrometer module;

a control voltage generator connected with the wearable solar battery module;

a second diode connecting the control voltage generator with the spectrometer module;

a second switch connected with the wearable solar battery module;

a transistor, of which the gate is connected with the control voltage generator and the drain or source is connected with the second switch;

a third diode connecting the source or the drain of the transistor with the spectrometer module;

a third switch connecting the control voltage generator with the spectrometer module;

a fourth switch connected with the wearable solar battery module; and a fourth diode connecting the fourth switch with the spectrometer module.

13. The solar bioelectrical impedance spectrometer of claim 12, wherein the battery management module is connected with the second diode and the control voltage generator.

14. The solar bioelectrical impedance spectrometer of claim 12, wherein the microprocessor module is configured to calculate a reference voltage value according to the output voltage of the wearable solar battery module and determine and control on/off states of the first switch, the second switch, the third switch and the fourth switch according to the reference voltage value.

15. The solar bioelectrical impedance spectrometer of claim 12, wherein when the reference voltage value is lower than a first voltage threshold, the microprocessor module is configured to turn on the first switch and turn off the other three switches at the same time.

16. The solar bioelectrical impedance spectrometer of claim 12, wherein when the reference voltage value reaches or exceeds the first voltage threshold and is lower than a second voltage threshold, the microprocessor module is configured to turn on the fourth switch and turn off the other three switches at the same time.

17. The solar bioelectrical impedance spectrometer of claim 12, wherein when the reference voltage value reaches or exceeds the second voltage threshold, the microprocessor module is configured to turn on the second switch and the third switch, and turn off the other two switches at the same time.

18. The solar bioelectrical impedance spectrometer of claim 11, wherein the impedance network analyzer comprises a 12-bit analog to digital converter (ADC) configured to sample and digitize the input signal at a rate of 1 MSPS and an integrated DSP configured to apply a Discrete Fourier Transformation (DFT) to the digitized input signal and return real and imaginary components of the transformed signal, and is configured to be programmed via an I2C bus.

19. The solar bioelectrical impedance spectrometer of claim 11, wherein the wide-band current source comprises:

a differential receiver amplifier with a first input, a second input and an output;

a unity gain amplifier connected between the second input of the differential receiver amplifier and the output of the differential receiver amplifier and forming a feedback loop; and an amplifier connected between the first input of the differential receiver amplifier and the output of the unity gain amplifier and forming a DC stable loop.

20. The solar bioelectrical impedance spectrometer of claim 19, wherein the wide-band current source further comprises two resistors and tetrapolar electrodes, output of the differential receiver amplifier and output of the unity gain amplifier being coupled to the tetrapolar electrodes through the two resistors respectively.

\* \* \* \* \*